(12) United States Patent
Kennard et al.

(10) Patent No.: US 8,617,115 B2
(45) Date of Patent: Dec. 31, 2013

(54) APPARATUS FOR UMBILICAL CATHETER

(76) Inventors: Clay Kennard, Oklahoma City, OK (US); James A. Harrison, Dallas, TX (US)

(*) Notice: Subject to any disclaimer, the term of this patent is extended or adjusted under 35 U.S.C. 154(b) by 11 days.

(21) Appl. No.: 13/109,835

(22) Filed: May 17, 2011

(65) Prior Publication Data

US 2011/0282290 A1   Nov. 17, 2011

Related U.S. Application Data

(60) Provisional application No. 61/345,509, filed on May 17, 2010, provisional application No. 61/384,267, filed on Sep. 18, 2010.

(51) Int. Cl.
*A61M 5/32* (2006.01)
(52) U.S. Cl.
USPC .................... 604/174; 604/177; 604/180
(58) Field of Classification Search
USPC ............... 604/174, 177, 179, 180; 600/249
See application file for complete search history.

(56) References Cited

U.S. PATENT DOCUMENTS

| | | | | |
|---|---|---|---|---|
| 5,370,627 A * | 12/1994 | Conway | ............ | 604/180 |
| 6,866,652 B2 * | 3/2005 | Bierman | ............ | 604/180 |
| 7,766,880 B1 * | 8/2010 | Spinoza | ............ | 604/174 |
| 7,799,001 B2 * | 9/2010 | Bierman | ............ | 604/180 |
| 2007/0142784 A1 * | 6/2007 | Dikeman et al. | ............ | 604/174 |

* cited by examiner

*Primary Examiner* — Kevin C Sirmons
*Assistant Examiner* — Imani Hayman
(74) *Attorney, Agent, or Firm* — James Harrison

(57) ABSTRACT

A medical catheter or tube clamp or support structure that is secured to an infant and holds a medical tube in place to prevent the tube from pistoning (axially moving within the infant relative to the entry point). In one embodiment, the medical tube claim comprises a catheter securing system that further includes a base that further includes at least one base member, a tube support member integrally formed with at least one base member that allows the tube to be inserted into an umbilical cord or stub in a relationally secure manner to prevent the tube from pistoning within an infant, and at least one channel for receiving a tube or catheter of a specified size and for securely holding the tube or catheter.

19 Claims, 14 Drawing Sheets

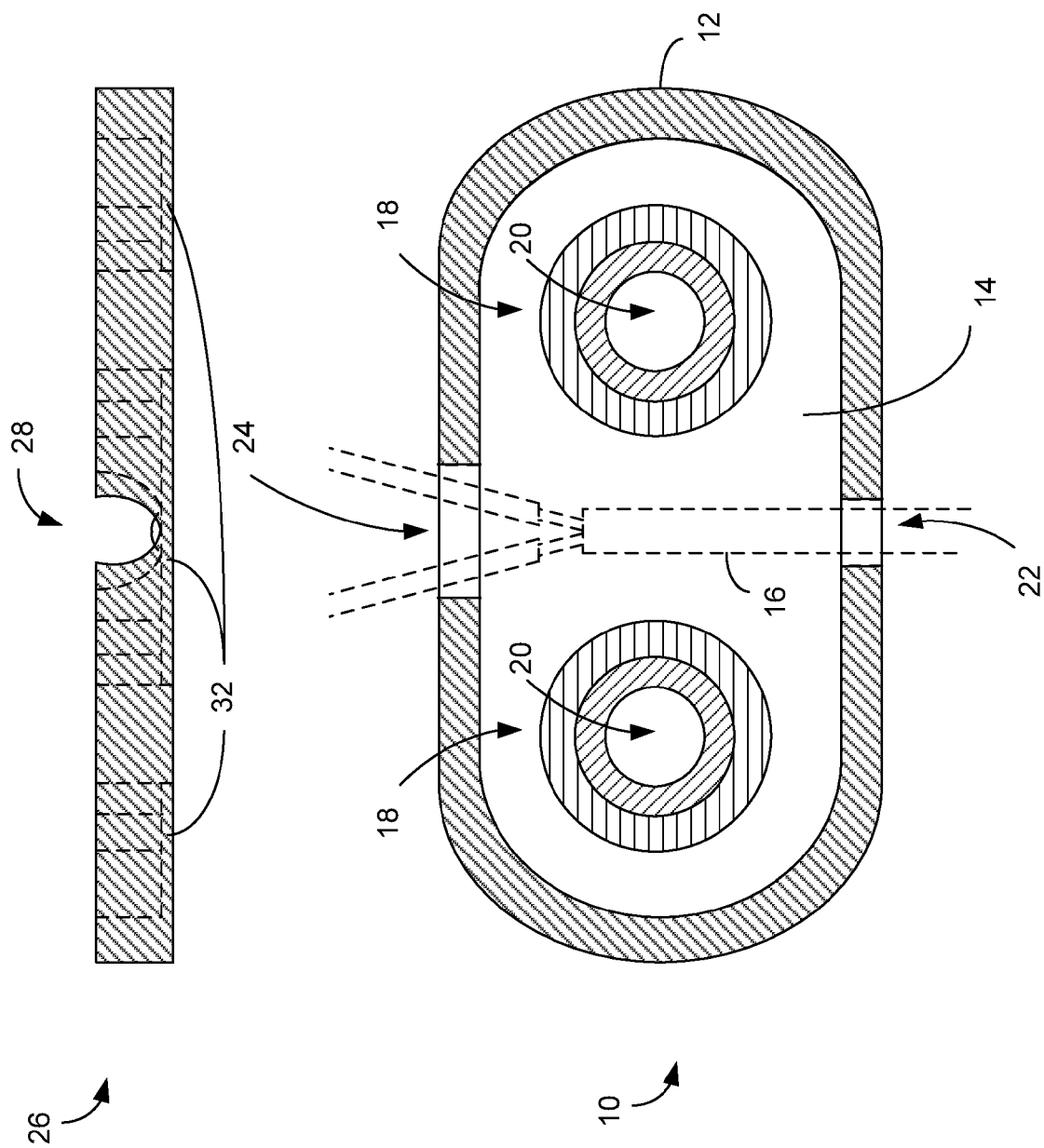

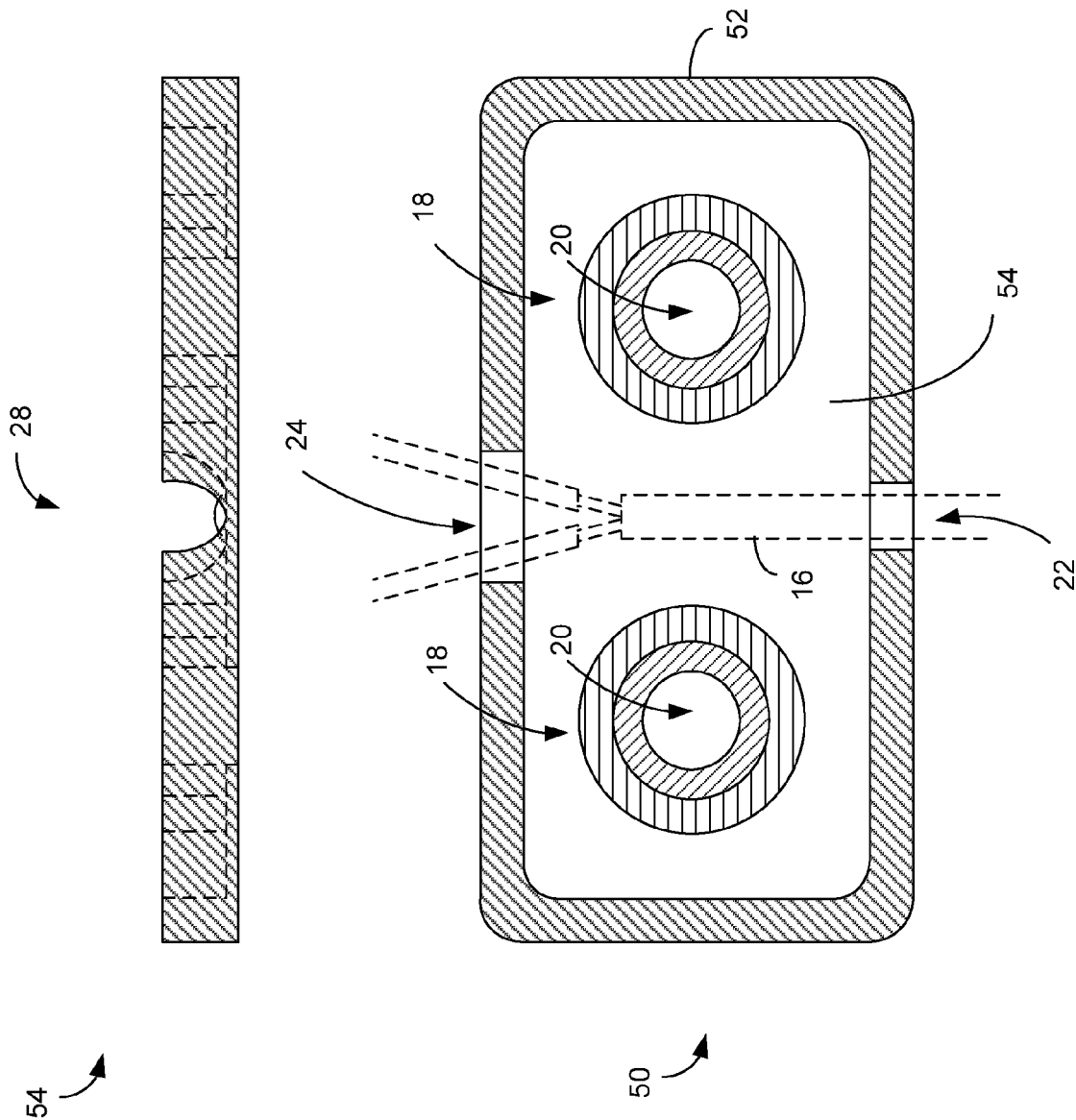

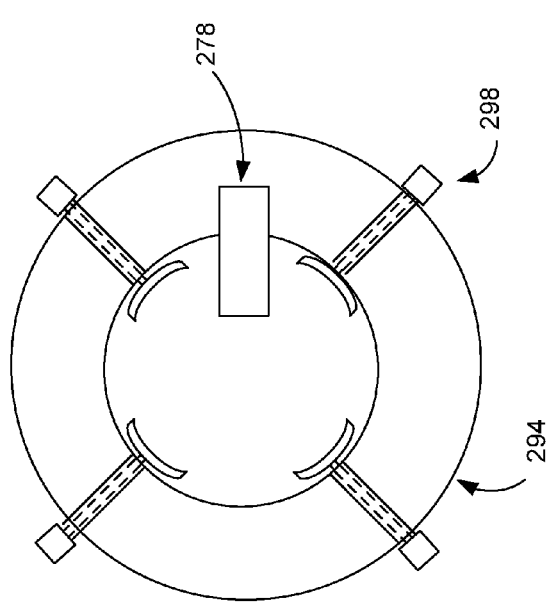
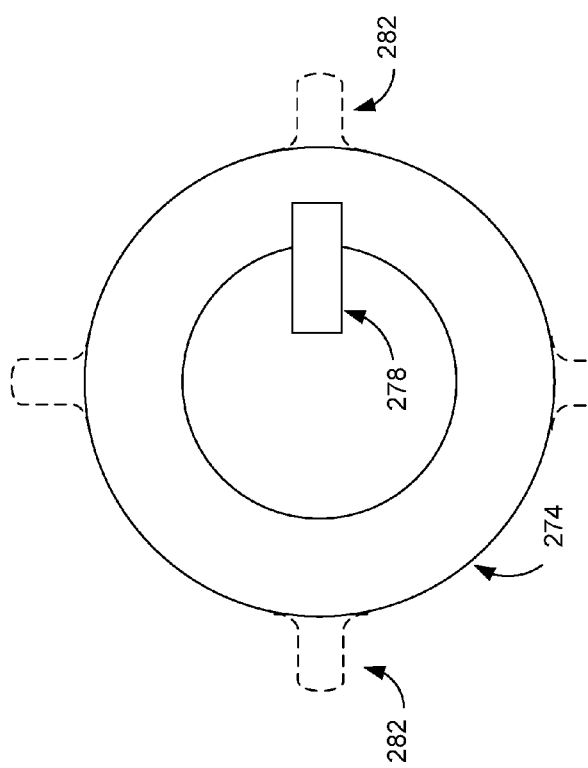
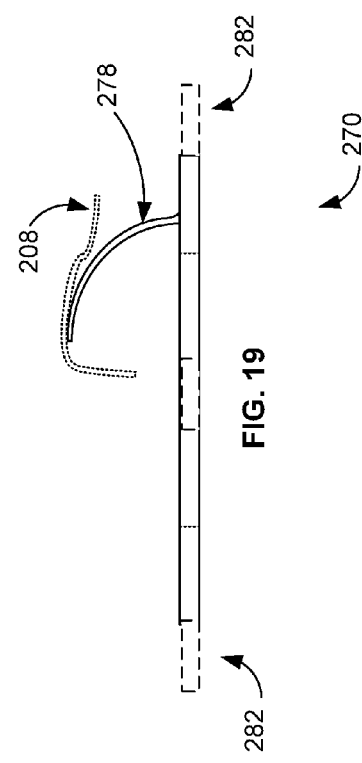

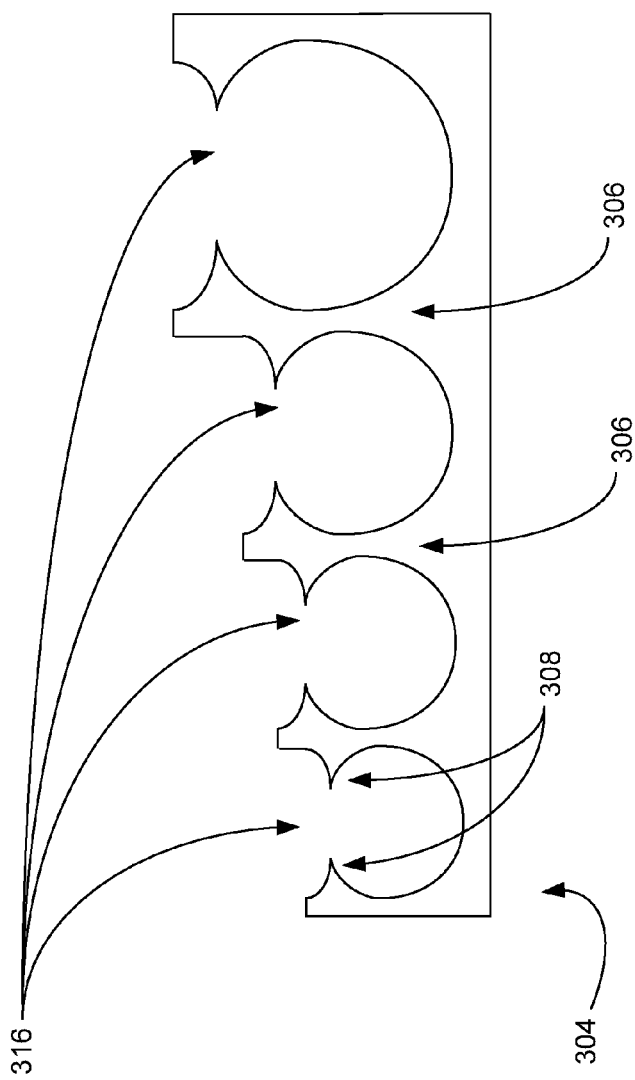
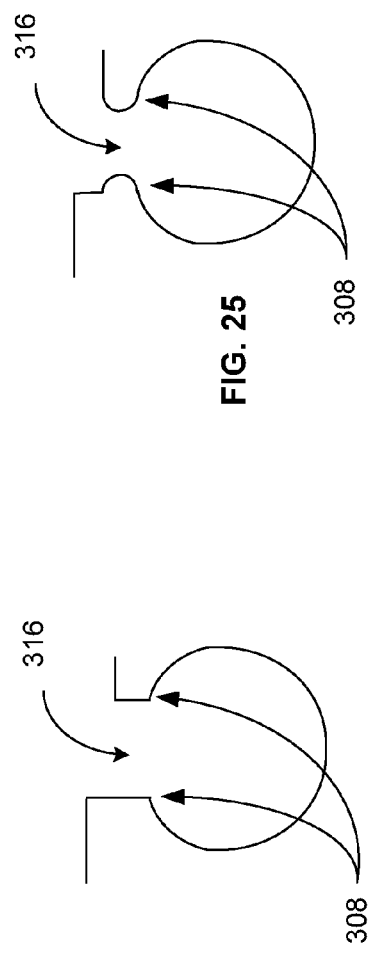
FIG. 23
FIG. 25
FIG. 24

APPARATUS FOR UMBILICAL CATHETER

CROSS REFERENCE TO RELATED PATENTS/PATENT APPLICATIONS

Provisional Priority Claim

The present U.S. Utility Patent Application claims priority pursuant to 35 U.S.C. §119(e) to the following U.S. Provisional Patent Applications which are hereby incorporated herein by reference in their entirety and made part of the present U.S. Utility Patent Application for all purposes:

1. U.S. Provisional Patent Application Ser. No. 61/345,509, entitled "APPARATUS FOR UMBILICAL CATHETER," filed May 17, 2010, pending.
2. U.S. Provisional Patent Application Ser. No. 61/384,267, entitled "APPARATUS FOR UMBILICAL CATHETER," filed Sep. 18, 2010, pending.

BACKGROUND

1. Technical Field

The present invention relates to medical devices and, more particularly, to fluid vessels for delivery of medicinal and nutritional flows and for draining fluids from a patient.

2. Related Art

Fluid delivery systems are known to fill a great necessity for delivery of medicine and nutrients to ill and disabled patients in many settings especially hospitals and health care facilities as well as for draining fluids. For example, in neonatal units, infants are often fed enterally (e.g., a tube inserted in the mouth or nasal opening and through the trachea for delivery of the fluid to the stomach or intestinal region of the body) and are also provided medication and other fluids intravenously. Medical tubes that are inserted into a patient's body cavity, vessel or duct are known as catheters. Catheters are often used for draining urine and other undesired fluids as well as for administering medication, nutrition, etc.

One challenge for delivery of fluids is that there exists a need for maintaining a particular fluid vessel such as a medical tube or catheter in a fixed location in relation to an entry point of the infant or patient. Tubing that shifts or withdraws can injure the patient whether the patient is an adult or an infant. The shifting of a tube often occurs in a reciprocating manner as a patient moves. Such motion in and out of the body is known as pistoning. The shifting of a tube, whether pistoning or just in one direction into the patient can, in the case of an infant having a catheter inserted through the umbilical stub, pierce the heart and kill the infant. Thus, often, medical tape is used to hold such umbilical catheters in place. The inventor has noted, however, that medical tape for this purpose is not reliable and an improved system would be desirable.

SUMMARY OF THE INVENTION

The present invention is directed to apparatus and methods of operation that are further described in the following Brief Description of the Drawings, the Detailed Description of the Invention, and the claims. Other features and advantages of the present invention will become apparent from the following detailed description of the invention made with reference to the accompanying drawings.

BRIEF DESCRIPTION OF THE DRAWINGS

A better understanding of the present invention can be obtained when the following detailed description of the preferred embodiment is considered with the following drawings, in which:

FIG. 3 is a top view of a medical tube clamp according to one embodiment of the invention.

FIG. 4 is a side view of the medical tube clamp of FIG. 1 according to one embodiment of the invention.

FIGS. 6 and 7 illustrate an alternative embodiment of the two-piece medical tube clamp of FIGS. 3 and 4.

FIGS. 18-19 illustrate another embodiment of a catheter support structure that supports a tube in a vertical position relative to an infant that has a circular base member that circumvents an umbilical stub or cord.

FIG. 20 illustrates another embodiment of a catheter support structure that supports a tube in a vertical position relative to an infant that has a circular base member that circumvents an umbilical stub or cord and that has clamps to clamp the support structure to the umbilical cord or stub.

FIG. 23 is a cutaway view of one end of a support member to illustrate one embodiment of the flanges and the securing tabs that combine to define the channels for holding an umbilical catheter.

FIGS. 24 and 25 are cutaway views that illustrate alternative embodiments of the flanges and tabs that define the channels for holding an umbilical catheter.

DETAILED DESCRIPTION OF THE DRAWINGS

Figure 1:
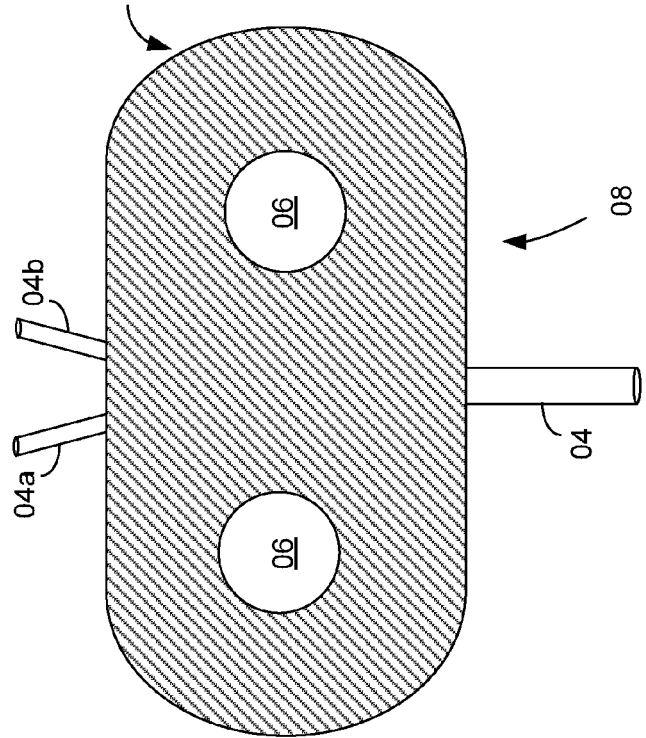
FIG. 1 is a top view of a medical tube with an integrally formed clamp for securing the medical tube into a fixed location in relation to the patient according to one embodiment of the invention.

FIG. 1 is a top view of a medical tube with an integrally formed clamp for securing the medical tube into a fixed location in relation to the patient according to one embodiment of the invention. A medical tube 02 includes a primary tube 04 and two secondary tubes 04a and 04b for conducting fluids. As may be seen, tubes 04a and 04b are fluidly coupled to tube 04. Thus, for example, if tubes 04a and 04b are conducting fluid from a patient, such fluid flows out of primary tube 04. As may also be seen, medical tube 02 includes two eyelets 06 within an integrally formed clamp 08 that allow the medical tube 02 to be stapled or sutured to the patient to keep medical tube 02 in a relatively fixed location.

Figure 2:
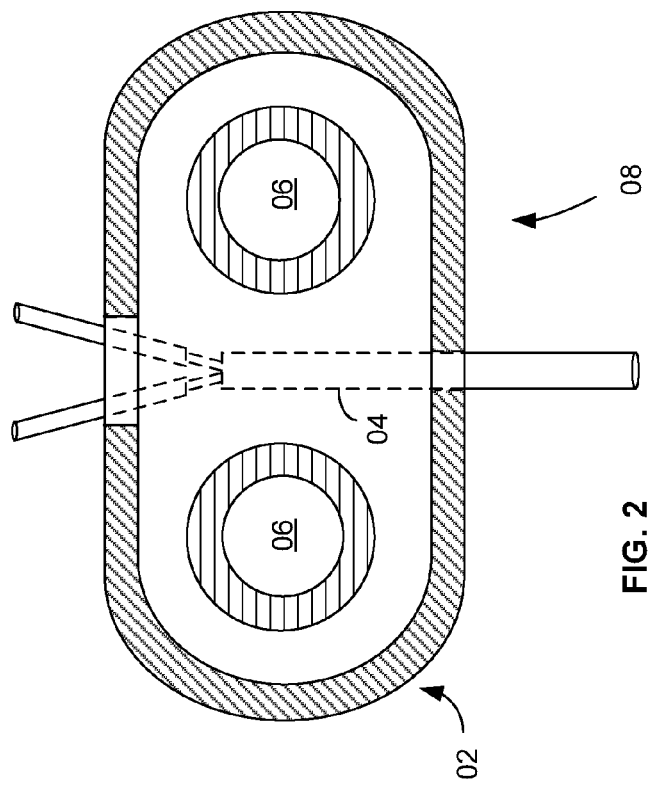
FIG. 2 is a cutaway top view of a medical tube with an integrally formed clamp for securing the medical tube into a fixed location in relation to the patient according to one embodiment of the invention.

FIG. 2 is a cutaway top view of a medical tube with an integrally formed clamp for securing the medical tube into a fixed location in relation to the patient according to one embodiment of the invention. Generally, FIG. 2 illustrates that the medical tube 02 comprises a reinforced perimeter of claim 08 and about the eyelets 06 to structurally reinforce clamp 08 of medical tube 02.

Generally, it may be seen that the integrally formed tube clamp 08 may be considered to be reinforced tabs that extend outwardly from a medical tube with eyelets to secure the medical tube 02 to the patient. The present specification and claims use the term "tube clamp" however, because, in other embodiments, the "tube clamp" is not formed integrally with the medical tube and is used to securely hold a tube (e.g., a catheter tube) to the patient. These tube clamps comprise one embodiment of a catheter securing structure.

FIG. 3 is a top view of a medical tube clamp 10 according to one embodiment of the invention. Medical tube clamp 10 is a medical device for attaching a tube into a fixed position in relation to a patient such as, for example, an infant. Medical tube clamp 10 is a two-piece device that includes a lower portion and an upper portion that matingly engage with each other about a tube such as a feeding tube to hold the tube in place. The lower piece includes a perimeter portion 12. The upper piece 14 is sized to fit within perimeter portion 12 in a snug manner to require some force or energy to be removed. Accordingly, if a tube 16 is laid on top of the lower portion and then upper portion 14 is snapped or push into mating engagement with the lower portion within perimeter portion 12, tube 16 is held in place. Medical tube clamp 10 includes two eyelets shown generally at 18. Eyelets 18 define an opening shown generally at 20. In the described embodiment, eyelets 20 allow medical tube clamp 10 to be medically attached by means of a stitch or staple to the infant or patient to hold medical tube clamp 10 in place in relation to the infant or patient. As may further be seen, medical tube clamp 10, and more particularly perimeter portion 12, define openings 22 and 24 to allow the tube 16 to enter/exit medical tube clamp 10.

FIG. 4 is a side view of the medical tube clamp 10 of FIG. 3 according to one embodiment of the invention. More particularly, defined openings 22 and 24 may readily be seen in side view 26 of FIG. 4 generally at 28 for allowing a tube such as tube 16 to enter/exit medical tube clamp 10.

Figure 5:
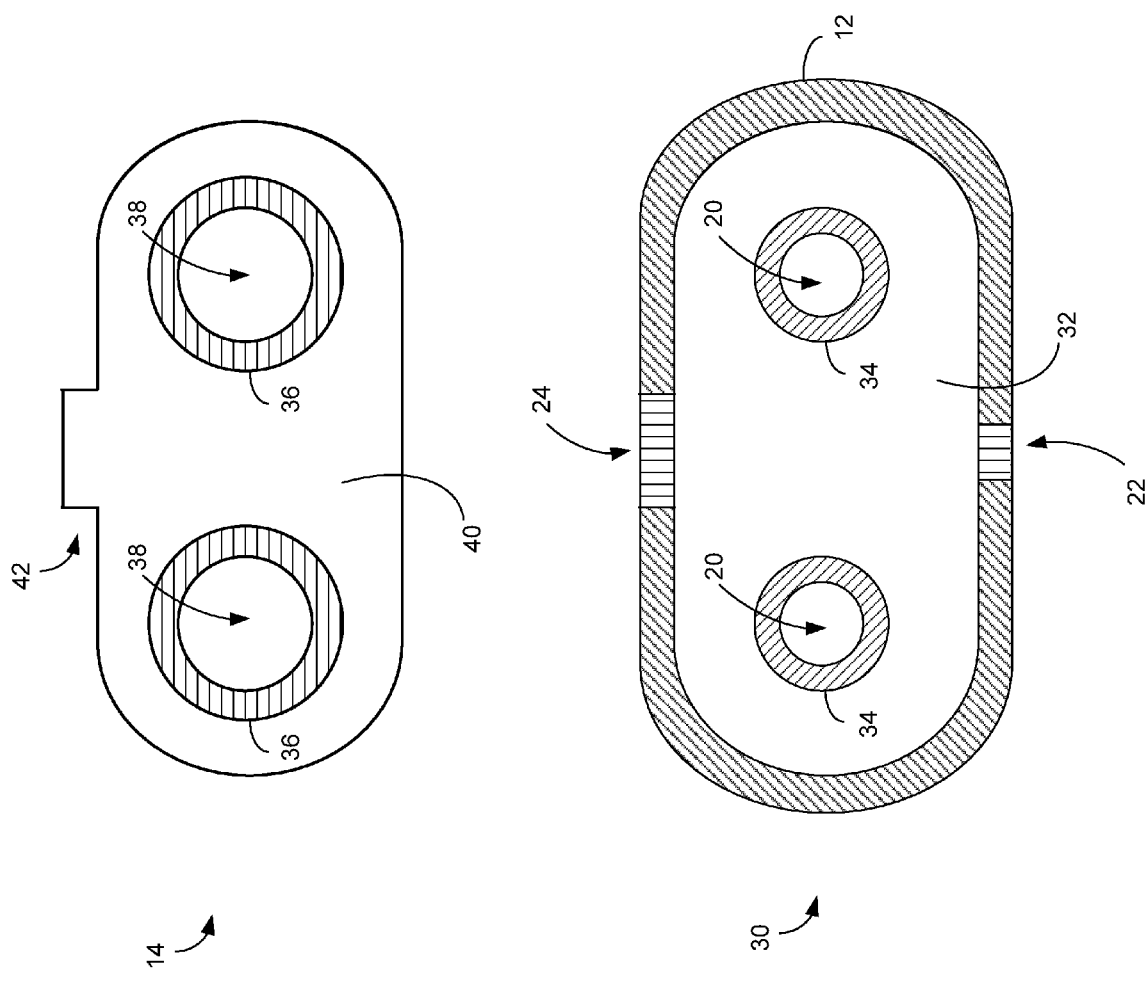
FIG. 5 is an exploded view of two piece device medical tube clamp according to one embodiment of the invention.

FIG. 5 is an exploded view of two piece device medical tube clamp 10 according to one embodiment of the invention. As described in relation to FIG. 3, medical tube clamp 10 included a lower portion, shown here at 30, and upper portion 14. Lower portion 30 includes perimeter portion 12 having defined openings 22 and 24. In one embodiment, lower portion 30 includes a floor 32 that is used to secure a tube such as tube 16. Eyelets 18 of FIG. 3 comprise an inner eyelet wall 34 and outer eyelet wall 36. As may be seen, inner eyelet wall 34 is formed as a part of lower portion 30 while outer eyelet wall 36 is formed as a part of upper portion 14. Eyelet wall 34 defines opening 20. Eyelet wall 36 defines opening 38 which is sized to matingly engage inner eyelet wall 34. Upper portion 14 includes a body 40 that further defines a tabbed portion 42 that is sized to matingly engage opening 24 of perimeter portion 12.

In operation, when upper portion 14 is matingly inserted within lower portion 30:

an inner wall of outer eyelet 36 engages an outer wall of inner eyelet 34;

tab 42 engages opening 24; and an outer perimeter of body 40 of upper portion 14 engages an inner wall of perimeter portion 12.

Accordingly, because the sizing of these elements within upper portion 14 and lower portion 30 and their associated eyelet walls are made to snugly and tightly fit with each other when upper portion 14 is engaged with lower portion 30, the two-piece medical tube clamp 10 operates to securely hold tube 16. Thus, when medical tube clamp-10 is properly fixed to the patient (e.g., infant), the tube remains in a fixed position in relation to the patient.

FIGS. 6 and 7 illustrate an alternative embodiment of the two-piece medical tube clamp 10 of FIGS. 1 and 2. As shown in FIG. 6, the two-piece devices is shown generally at 50 which includes a perimeter portion 52 and an upper portion 54 that shaped differently from their corresponding elements of FIGS. 3 and 4. A primary difference with the embodiment of FIGS. 6 and 7 is that medical tube clamp 50 is more square or rectangular in shape rather than having the more rounded ends as shown in FIG. 3. Thus, outer perimeter 42 and upper portion 54 are shaped differently than the corresponding elements 12 and 14 of FIGS. 3 and 4. Upper portion 54 having a body 62 thus is shaped to matingly engage with outer perimeter 52. As all other elements other than the shape of the device and outer perimeters are the same as in FIGS. 3 and 4, such common elements won't be described again. It should also be noted that other shapes may be used without deviating from the concepts of the embodiments of the present invention. For example, eyelets 18 may also be formed in a non-circular shape (e.g., substantially square, rectangular, oval, etc.).

Figure 8:
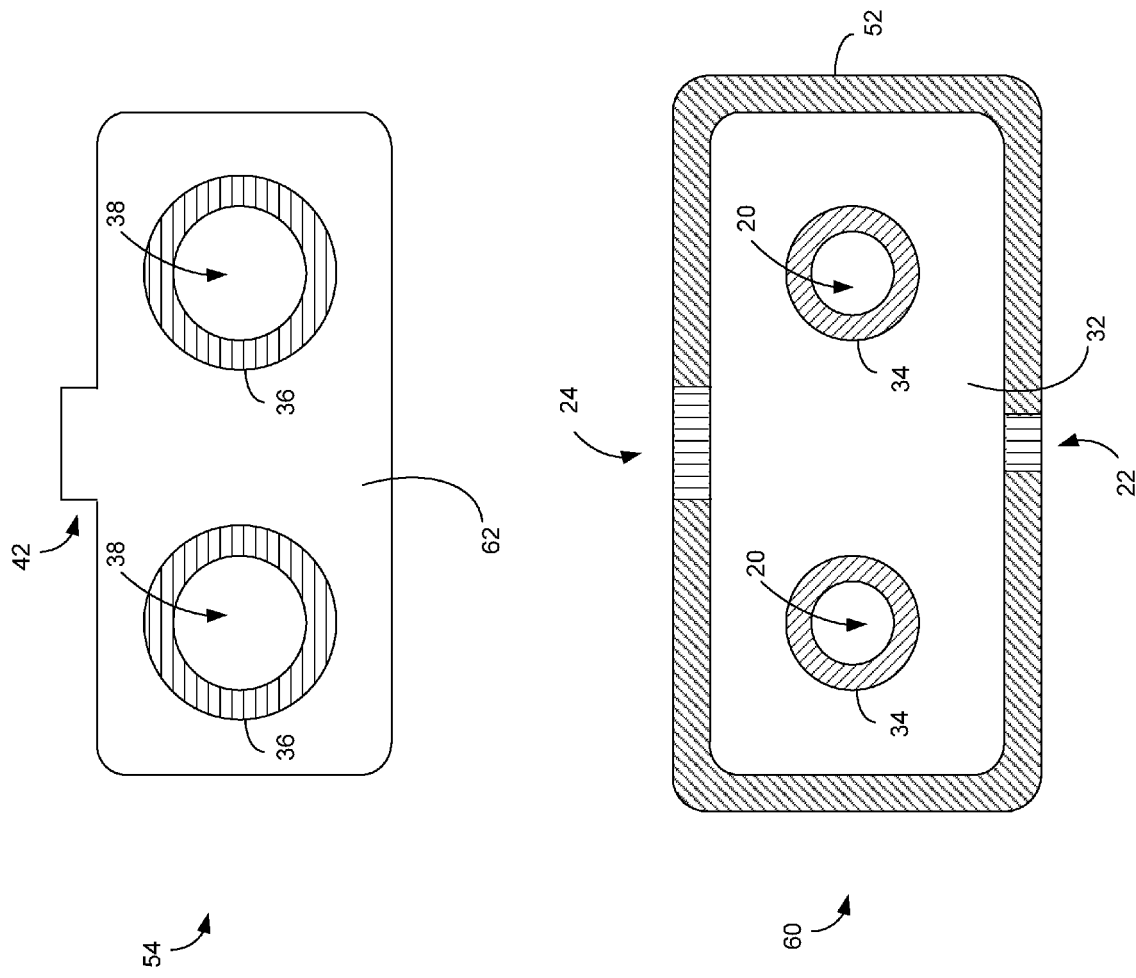
FIG. 8 is an exploded view of two piece device medical tube clamp according to one embodiment of the invention.

FIG. 8 is an exploded view of two piece device medical tube clamp 50 according to one embodiment of the invention. As described in relation to FIG. 6, medical tube clamp 50 included a lower portion, shown here at 60, and upper portion 54. Lower portion 60 includes perimeter portion 52 having defined openings 22 and 24. In one embodiment, lower portion 60 includes a floor 32 that is used to secure a tube such as tube 16. Eyelets 18 of FIG. 3 comprise an inner eyelet wall 34 and outer eyelet wall 36. As may be seen, inner eyelet wall 34 is formed as a part of lower portion 60 while outer eyelet wall 36 is formed as a part of upper portion 54. Eyelet wall 34 defines opening 20. Eyelet wall 36 defines opening 38 which is sized to matingly engage inner eyelet wall 34. Upper portion 54 includes a body 62 that further defines a tabbed portion 42 that is sized to matingly engage opening 24 of perimeter portion 52.

In operation, when upper portion 54 is matingly inserted within lower portion 60:

an inner wall of outer eyelet 36 engages an outer wall of inner eyelet 34;

tab 42 engages opening 24; and an outer perimeter of body 62 of upper portion 54 engages an inner wall of perimeter portion 12.

Accordingly, because the sizing of these elements within upper portion 54 and lower portion 60 and their associated eyelet walls are made to snugly and tightly fit with each other when upper portion 54 is engaged with lower portion 60, the two-piece medical tube clamp 50 operates to securely hold tube 16. Tube 16, therefore, remains in a fixed position in relation to the patient when medical tube clamp 50 is attached to the patient (e.g., an infant).

Figure 9:
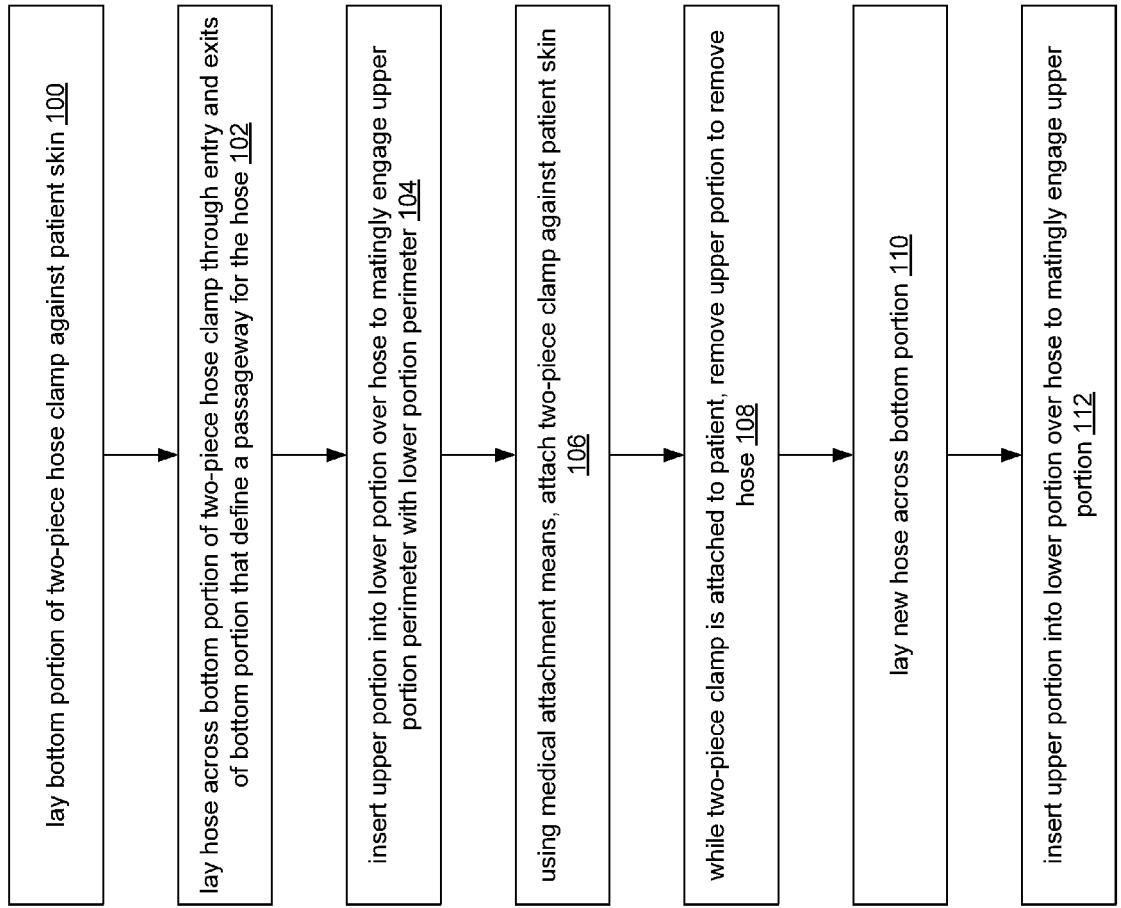
FIG. 9 is a flow chart of a method according to one or more embodiments of the invention.

FIG. 9 is a flow chart of a method according to one or more embodiments of the invention. The method includes laying a bottom portion of a two-piece tube clamp against a patient's skin (100). Thereafter, the method includes laying a medical tube (e.g., a feeding tube) across a bottom portion of two-piece tube clamp through entry and exits of the bottom portion that define a passageway for the tube (102). Thereafter, the method includes inserting an upper portion of the two-piece tube clamp over the tube and into the lower portion of the two-piece tube clamp to matingly engage the upper portion perimeter with the lower portion perimeter (104). The method also includes, using medical attachment means, attaching the two-piece clamp against patient skin (106). Medical attachment means include medical staples, stitches, etc.

While the two-piece clamp is attached to the patient, an alternative embodiment of the inventive method includes removing the upper portion of the two-piece tube clamp to remove tube (108). Thereafter, the method includes laying new tube across bottom portion of the two-piece tube clamp (110) and inserting the upper portion into lower portion over the new tube to cause the upper portion to matingly engage the lower portion (112). In one embodiment, this step includes pushing anchors of one of the top and bottom portions of the two-piece tube clamp into anchoring ports of the other of the top and bottom portions of the two-piece tube clamp. For example, if the anchors are formed integrally with the upper portion and extend outwardly therefrom and if the anchoring ports are formed within the lower portion, the method includes pushing the upper portion into a defined space of the lower portion and also pushing the outwardly protruding anchors into the anchoring ports.

Figure 10:
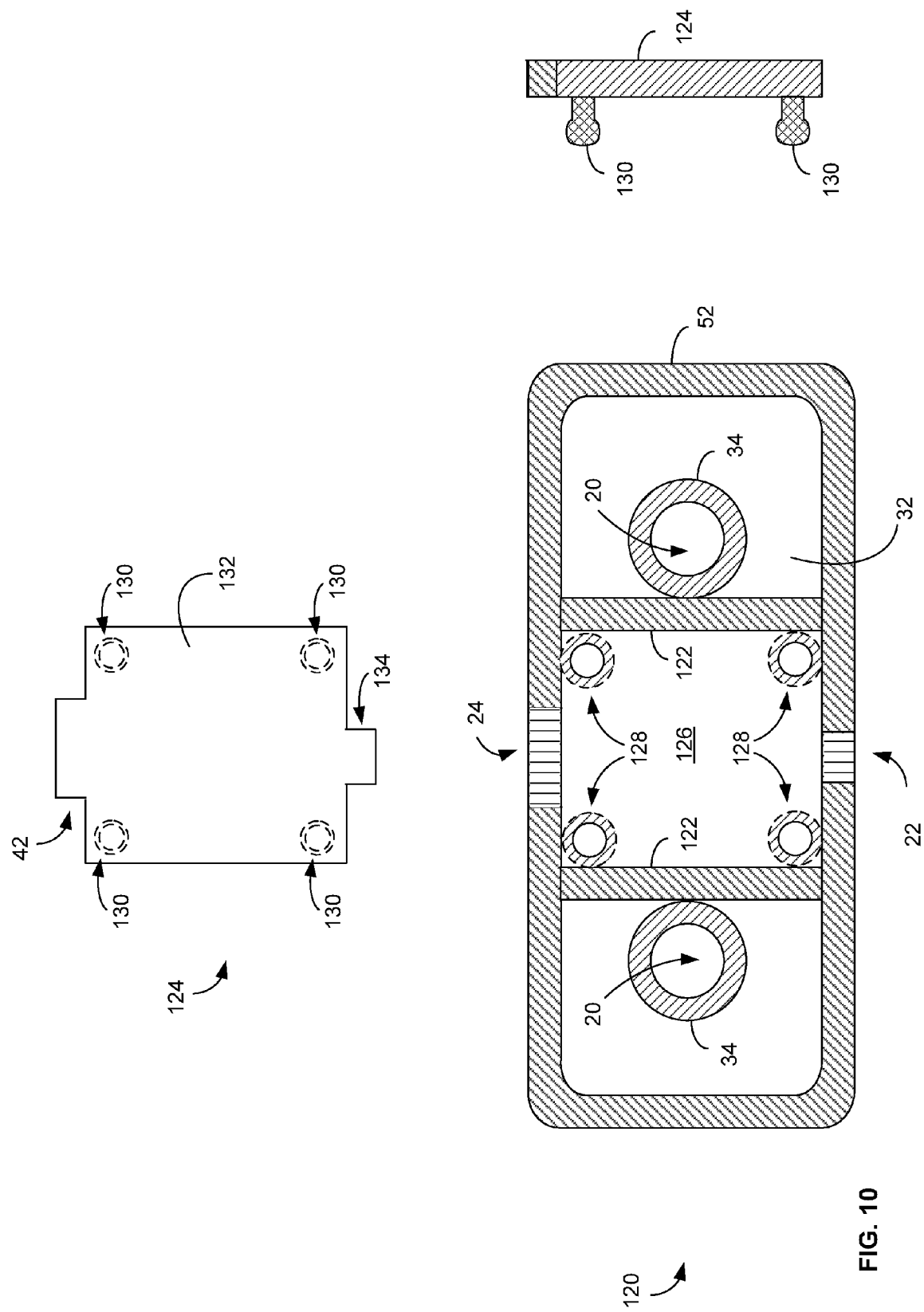
FIG. 10 is a two-piece medical tube clamp according to an alternative embodiment of the invention.

FIG. 10 is a two-piece medical tube clamp 120 according to an alternative embodiment of the invention. Medical tube clamp 120 includes internal walls 122 that, in cooperation with a portion of outer perimeter 52, receives upper portion 124 wherein upper portion 124 is sized to tightly fit within a space defined by internal walls 122 and outer perimeter 52. One advantage of the embodiment of FIG. 10 is that, after the two-piece medical tube clamp 120 has been attached to the patient, the upper portion may be removed to change the tube that is secured by two-piece medical tube clamp without disturbing the attachment of two-piece 120 to the patient.

In one embodiment of the invention, an upper portion locking system is used to further increase a strength of the mating engagement of the upper and lower portions of the two-piece medical tube clamp 120. In the described embodiment, a floor 126 of the lower portion of medical tube clamp 120 defines a plurality of anchoring ports 128 that are sized to receive and tightly hold a corresponding plurality of anchors 130 that protrude outwardly from a body 132 of upper portion 124.

In another embodiment of the invention, upper portion 124 includes a body 132 that further defines a tabbed portion 134 that is sized to matingly engage opening 22 of perimeter portion 52 while tabbed portion 42 matingly engages opening 24 of perimeter portion 52. It should be understood that tabbed portion 134 may also be included in other embodiments such as those illustrated in relation to each of the figures herein.

In premature and full term infants, a medical need often exists to insert a catheter or medical tube through the umbilical stump (e.g., into a vein) for a variety of purposes. Doing so, however, poses risks. If the catheter tube is not held in a stable manner, the tube may move within the infant along the vein with the adverse effect of damaging tissue that may endanger or fatally injure the infant. For example, the catheter tube may slide too deeply and pierce the infant heart. There also may be a need for adults to use a tube supporting structure that securely holds a tube and prevents pistoning.

Accordingly, there is a need for a structure (a tube structure that can clamp or secure a catheter tube) and a method for stabilizing a medical tube, such as a catheter tube, in relation to the infant even while an infant is moved for needed care or while the infant moves on its own accord. The various embodiments of the invention all include a catheter tube securing structure that stabilizes the catheter tube to prevent movement of the catheter in relation to the infant, or in other words, to prevent the tube from "pistoning" (sliding in and out) within the infant vein or other anatomical element.

Figure 12:
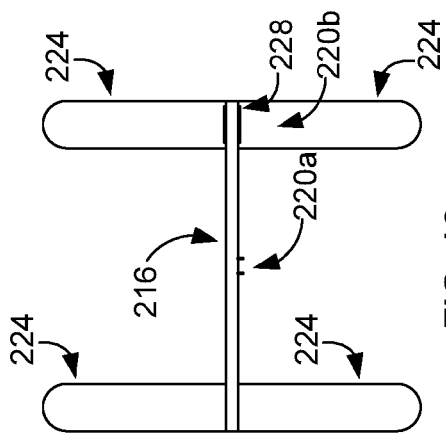
FIGS. 11-13 illustrate one embodiment of a tube support structure that supports a tube in a vertical position relative to an infant.
Figure 13:
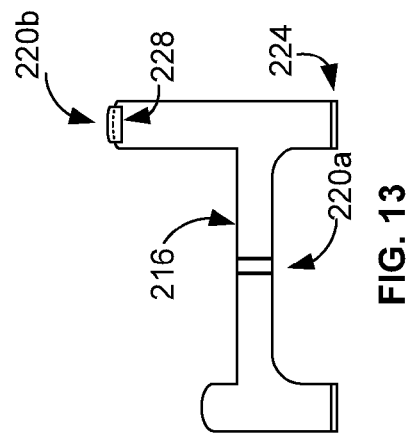
Figure 11:
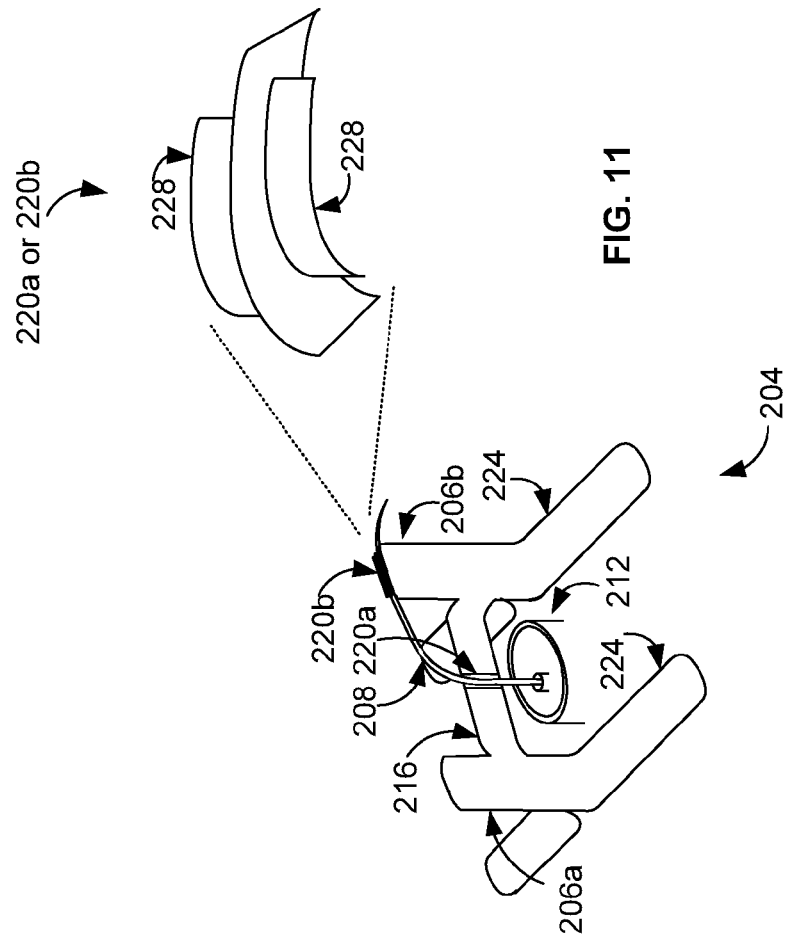

FIGS. 11-13 illustrate one embodiment of a catheter support structure that supports a tube in a vertical position relative to an infant. Referring to FIG. 11, a catheter securing structure 204 is shown for stabilizing a catheter tube 208 that is placed into an umbilical cord or stub 212. Catheter securing structure 204 includes two upwardly extending support members 206a and 206b and a supporting beam 216 that extends between the two support members 206a-b. Structure 204 also includes securing elements 220a and 220b for securing tube 208. Structure 204 further includes base members 224 having rounded corners. In this embodiment, the base members 224 extend outwardly across the infant body and may be taped or secured to the infant with a wrap to secure the structure 204 about the umbilical cord 212 to securely hold tube 208 in place. This, therefore, stabilizes the tube in relation to the infant to prevent pistoning.

The embodiment of FIG. 11 includes securing elements 220a-b to secure the tube or catheter 208 to structure 204 in a desired manner. In one embodiment, as is shown in the expanded view of the securing elements 220a-b having outwardly extending flanges 228, the tube is axially aligned to a direction parallel to the flanges 228 of securing elements 220a-b. The flanges 228 of the securing elements 220a-b may be formed to securely receive a tube of a specified size. In one embodiment, flanges 228 of securing elements 220a-b are shaped with tabs to receive and hold tube 208. Alternatively, flanges 208 may be used to guide the tube in a specified direction with the intention that an adhesive would be used to securely affix the tube to the structure. For example, a piece of tape may be used to secure the tube 208 to structure 204. A channel defined by flanges 228 is sized to receive and hold the tube to the structure. As should also be noted, securing element 220a is oriented to direct the medical tube substantially vertically in relation to an infant laying on its back. More specifically, when the structure 204 is attached or affixed to the infant, the tube is held in a perpendicular direction relative to the torso of the infant by securing element 220a.

FIG. 12 is a top view of securing structure 204 according to one embodiment of the invention. FIG. 11 shows, for example, the beam 216, the securing elements 220a and 220b, and the flanges 228. FIG. 12 also shows the base members 224. FIG. 13 shows a front view of securing structure 204 showing the same elements as FIGS. 11-12. As may be seen in the embodiment of FIG. 13, the two upwardly extending support members 206 (206a and 206b) are sized differently. Here, support member 206a is shorter in length than support member 206b. Support member 206b is formed to extend a necessary amount beyond beam 216 so that medical tube 208 may readily bend between securing elements 220a-b without kinking as it changes direction to be vertically oriented by the securing element 220a to be directed into the umbilical stub 212.

Figure 14:
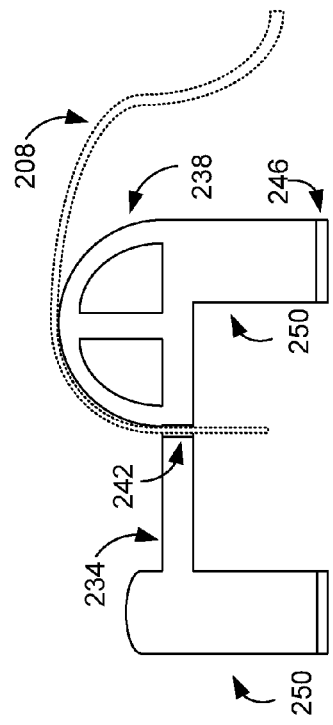
FIGS. 14-15 illustrate another embodiment of a catheter support structure that supports a tube in a vertical position relative to an infant.
Figure 15:
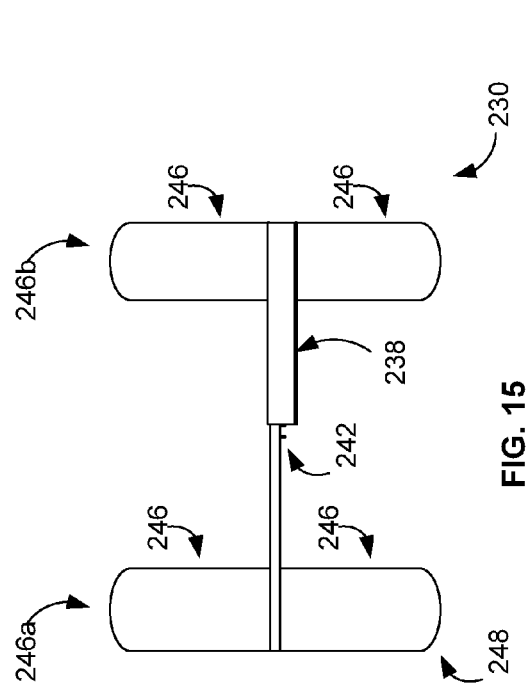

FIGS. 14-15 illustrate another embodiment of a catheter securing structure that supports a tube in a vertical position relative to an infant. FIG. 14 illustrates a front view while FIG. 15 illustrates a top view of the tube support structure. Referring to FIG. 14 and FIG. 15, a catheter securing structure 230 is shown for stabilizing a catheter tube 208 that is placed into an umbilical cord or stub. Catheter securing structure 230 includes a supporting beam 234 and securing elements 242 for securing tube 208. Structure 230 further includes base members 246 having rounded corners 248. In this embodiment, the four base members 246 extend outwardly across the infant body and may be taped to the infant or wrapped to secure the structure 230 about the umbilical cord or stub (not shown here) to securely hold tube 208 in place to stabilize the tube in relation to the infant to prevent pistoning of the tube. As may be seen, a first pair of base members 246, shown at 246a, extend planarly and away from each other.

Figure 16:
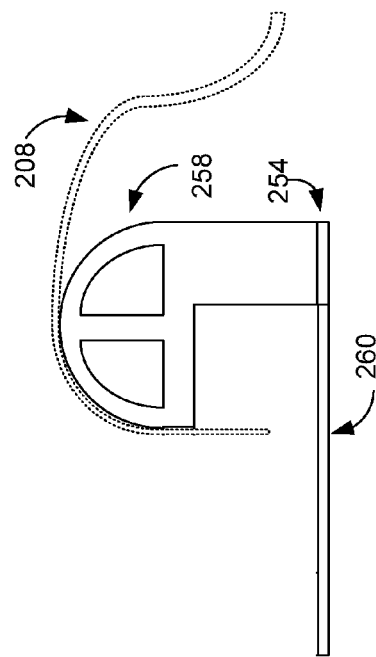
FIGS. 16-17 illustrate another embodiment of a catheter support structure that supports a tube in a vertical position relative to an infant.
Figure 17:
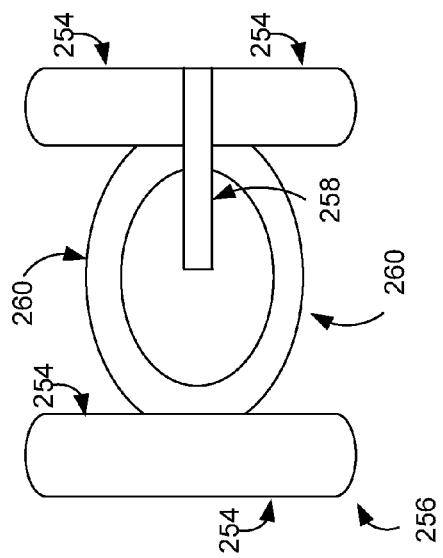

Each of a second pair of base members 246, shown at 246b, also extends planarly relative to the infant and away from each other. The two pairs of base members shown at 246a and 246b are on opposite sides of structure 230 and are structurally connected only by supporting beam 234 that extends between two upwardly extending support members 250. The two upwardly extending support members 250 extend upwardly from the two pairs of base members 246 shown at 246a and 246b, respectively. Additionally, this embodiment includes a tube support member 238 that allows a medical tube or catheter to be securely held in place and to guide the medical tube or catheter into the umbilical stub or cord in a perpendicular manner relative to the infant body. In one embodiment, support member 238 includes securing elements 242 similar to flanges 228 that are formed thereon to secure and guide tube 208 into a vertical position (relative to the infant and stub 212 (not shown here) without kinking or bending tube 208 in a manner that fluid flow is inhibited. In the embodiment of FIGS. 16-17, however, the outer surface of tube support member 238 is sufficiently wide in relation to the tube to hold the tube in place with some tape. Alternatively, support member 238 may include flanges that define a channel that receives and securely holds tube 208.

FIGS. 16-17 illustrate another embodiment of a catheter support structure that supports a tube in a vertical position relative to an infant. Referring to FIGS. 16-17, a catheter securing structure 252 is shown for stabilizing a catheter tube 208 that is placed into an umbilical cord or stub 212 (not shown here in FIGS. 16 and 17). FIG. 16 illustrates a front view while FIG. 17 illustrates a top view of the catheter securing structure. Structure 252 further includes base members 254 having rounded corners 256. A tube or catheter support member 258 is similar to tube support member 238 of FIGS. 14-15. In this embodiment, a circular or ringed base member 260 extends outwardly across the infant body and may be taped to the infant to secure the structure 252 about the cord or stub 212 (not shown here) to securely hold tube 208 in place to stabilize the tube in relation to the infant to prevent pistoning.

Tube support member 258 allows a tube or catheter to be affixed to securely hold the tube or catheter and to guide the tube or catheter into the umbilical stub or cord in a perpendicular manner relative to the infant body. In one embodiment, support member 258 includes securing flanges that are formed thereon to secure and guide tube 208 into a vertical position (relative to the infant and stub 212 (not shown here) without kinking or bending tube 208 in a manner that fluid flow is inhibited. In the exemplary embodiment of FIGS. 16-17, however, support member 258 does not include the securing flanges. Rather, it is sized to allow the catheter or tube to be taped to the support member while securely holding the catheter or tube in a manner that guides the tube or catheter into a vertical orientation in relation to the infant to enter the umbilical cord or stub.

In contrast to other catheter securing structures, described in relation to prior figures, structure 252 does not include a supporting beam. Structure 250 does include, however, the circular base ring 260 that assists with stabilizing the catheter securing structure 252 against the infant for stabilizing tube 208. As may be seen, base ring 260 is sized to circumvent the umbilical stub or cord (after it has been cut). Here, ring 260 creates a structural coupling between the opposed pairs of base members 254 instead of a such structural coupling being achieved by way of a beam as described before.

FIGS. 18-19 illustrate another embodiment of a catheter support structure that supports a tube relative to an infant or patient that includes a circular base member that circumvents an umbilical stub or cord or point of entry. Referring to FIG. 18, a top view of a catheter securing structure 270 is shown which comprises a circular base ring 274 characterized by a sufficient width to securely hold structure 270 against the infant body. A tube support member 278 extends outwardly from base ring 274 and is shaped in a curvilinear manner to terminate in a substantially horizontal position relative to base ring 274 above the stub 212. Stub 212 is not shown here, but should be understood to be located within base ring 274. Tube support member 278 may optionally include securing flanges 282 for securely holding and guiding the catheter tube. Such securing flanges 282 would be similar to those described before. In such an alternative embodiment of structure 270, flanges 282 radiate outwardly from ring 274 to support taping the base ring 274 and structure 270 to the infant or patient.

FIG. 19 illustrates a side view of catheter support structure 270. As may be seen, tube 208 may be affixed to tube support member 278. It should be understood that tube support member 278 may readily be substituted for other shapes such as, for example, support member 258 of FIGS. 16-17.

FIG. 20 illustrates another embodiment of a catheter support structure that supports a tube relative to an infant or patient that has a circular base member and that circumvents an umbilical stub or cord or entry point and that has clamps to clamp the support structure to the umbilical cord or stub. Referring to FIG. 20, a catheter securing structure 290 comprises a circular base ring 294 characterized by a sufficient width to securely hold structure 290 against the infant body. A tube support member 278 similar to that of FIGS. 18 and 19 extends outwardly from base ring 294 and is shaped in a curvilinear manner to terminate the tube in an axial position above the stub 212 (not shown here). Additionally, as may be seen, structure 290 comprises a plurality of clamps 298 that may be used to clamp or secure structure 290 to the umbilical cord or stub. The clamps 298 are ratcheting type clamps in one embodiment. In another embodiment, as shown here, clamps 298 comprise a threaded bolt that may be screwed or turned to cause the clamps to be urged axially into or away from the umbilical cord or stub according to the direction the bolt is turned.

Figure 21:
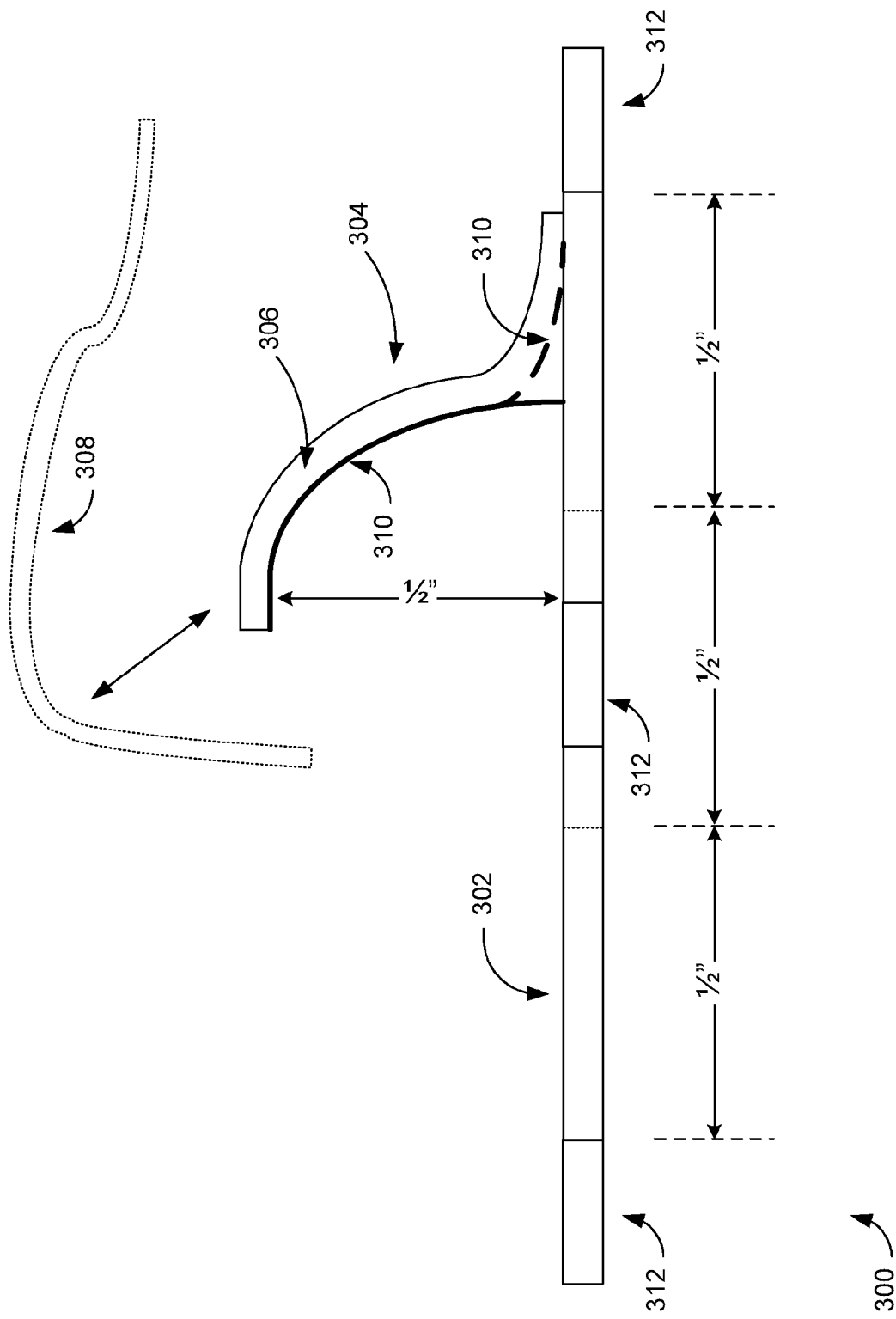
FIGS. 21 and 22 are side and top views, respectively, of a catheter support structure according to an embodiment of the invention.
Figure 22:
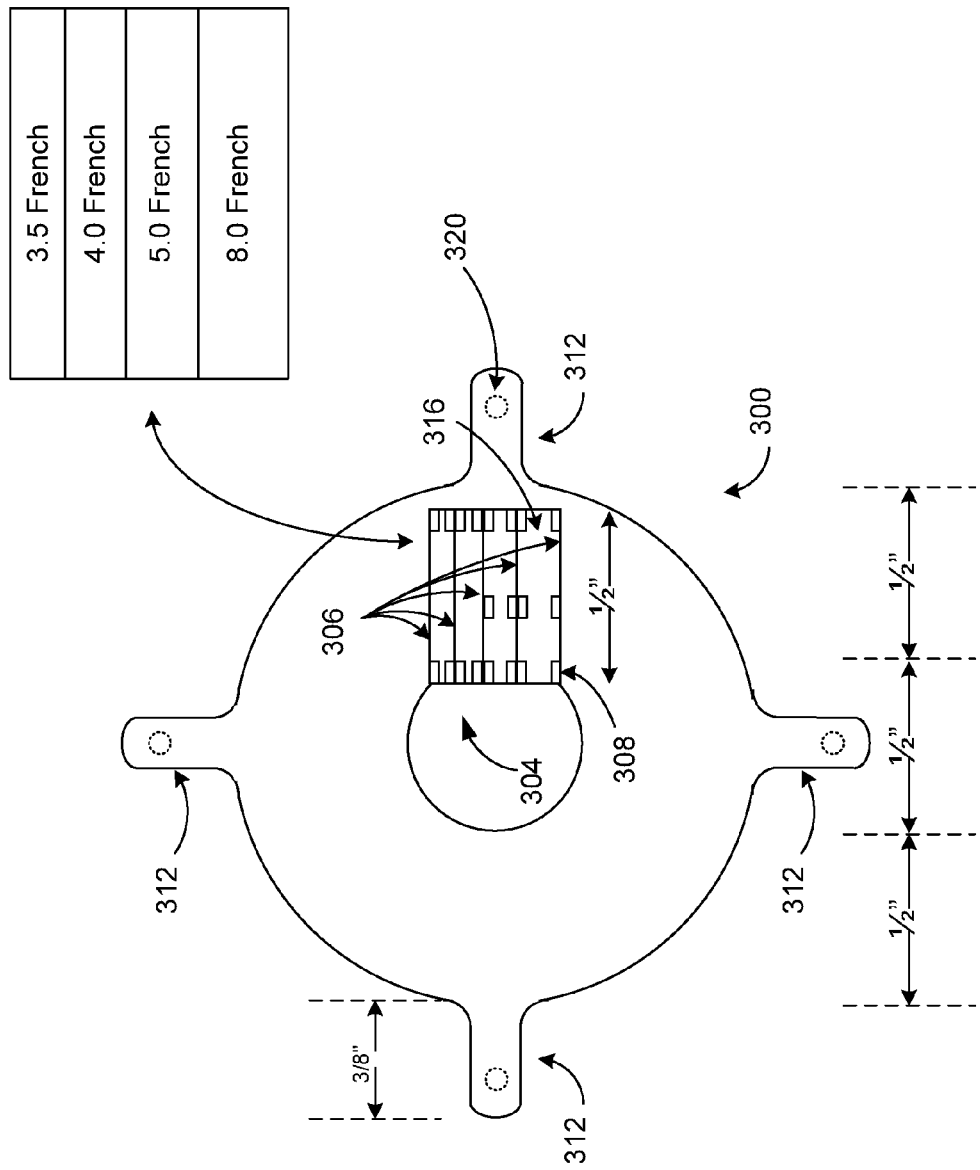

FIGS. 21 and 22 are side and top views, respectively, of a catheter support structure according to an embodiment of the invention. Referring to FIG. 21, a side view of a catheter support structure 300 is shown which comprises a circular base ring 302 characterized by a sufficient width to securely hold structure 300 against the infant or patient body. In the described embodiment, base ring 302 has a 1.5 inch total diameter forming an opening that is 0.5 inches wide. Thus, the ring itself is characterized by a ½ inch width. Stated more technically, an outer radius of the ring is 0.75 inches while an inner radius of the ring is 0.25 inches in one embodiment though alternative dimensions may be used. These dimensions are for one embodiment. The dimensions may readily be adjusted for other embodiments.

A tube support member 304 extends outwardly from base ring 302 and is shaped in a curvilinear manner to terminate in a horizontal position above the umbilical stub 212 (not shown here, but should be understood to be located within the opening of base ring 302) or, more generally, an entry point of the patient. Tube support member 304 includes five securing flanges 306 for securely holding and guiding the catheter tube 308 though or in between flanges 306. As is shown more clearly in FIG. 22, five flanges 306 extend outwardly from a base 310 of tube support member 304. As may further be seen, a peak height of base 310 of support member 304 is 0.5 inches above base ring 302. From that peak, base 310 curves towards base ring 302 and slopes into base ring 302 in a manner that a catheter tube 308 inserted within flanges 306 towards base 310 of support member 304 does not bend or kink in a manner that fluid flow is restricted. As may be seen in FIGS. 21-22, a plurality of outwardly extending tabs 312 extend outward from base ring 302 which tabs may be used to secure base ring 302 of structure 300 to the infant.

In the described embodiment, each of a plurality of tabs 312 extends ⅜" from base ring 312 (in one embodiment). These tabs 312 may, in one embodiment, be made to be structurally flexible for securing to the curved shape of the infant. While not shown explicitly, it should be noted that the various embodiments of the invention may include an overmold portion (especially if the securing structure such as tabs 312 is made of an inflexible material) to improve comfort and/or acceptance of the device by the infant. For example, at least the bottom portion or base portion of structure 300 may be overmolded with a flexible material (e.g., silicon) to render the support structure more comfortable.

While tabs 312 are shown to extend from vertical and horizontal axis' it should be understood that the orientation of tabs 312 may readily be changed. For example, the tabs 312 may be rotationally shifted by about 45 degrees to extend in a manner that there is no overlap between a tube extending from support member 304 and any one of the tabs 312. As may also be seen, tabs 312 may include openings or apertures 320 that allow the tabs to be sutured to another element, such as a gauze, to hold the securing structure in place. Alternatively, apertures 320 may be replaced with protruding bumps to create a surface tension with a gauze or other bandaging material to hold the securing structure 300 in place.

FIG. 22 illustrates a top view of securing structure 300. As may be seen, tube 308 may be secured to support member 304 by one of a plurality of channels defined by the spacing between the flanges 306. In the described embodiment, the five outwardly extending flanges are spaced to receive and secure only one of four specifically sized tubes. In the described embodiment, the flanges are disposed to create four channels that will securely hold, using the French Catheter scale, as is known by those of average skill in the art, 3.5, 4.0, 5.0 and 8.0 French Catheter scale tubes. A "1.0" of the French Catheter scale is approximately 0.33750 millimeters. It should be understood that support member 304 may be made to have more or less that 5 flanges 306 to form more or less than 4 channels that securely hold catheter tubes. Moreover, the flanges 306 may readily be disposed to form channels of different sizes to securely hold catheter tubes of different sizes. As may further be seen, each flange 306 includes at least two securing tabs 308 protruding inwardly towards the channels 316 formed by the flanges 306 to securely hold the catheter tubes. Moreover, the two widest channels 316 (the two "bottom channels") have at least three sets of securing tabs 308 for securely holding catheter tubes. More or less numbers of securing tabs 308 may be used. In one embodiment, the securing tabs 308 extend along the majority of the length of the channels 316 defined by flanges 306.

One aspect of the embodiment shown in FIGS. 21-22 is that catheter tubes made from either silicon or urethane may be securely held by securing structure 300, and, more specifically, by the combination of the channels 316 formed by the flanges 306 and the securing tabs 308.

FIG. 23 is a cutaway view of one end of support member 304 to illustrate one embodiment of the flanges 306 and the securing tabs 308 that combine to define the channels 316. As may be seen, securing tabs 308 extend planarly towards each other and away from flanges 306. Moreover, tabs 308 and flanges 306 are shaped to form a passage way or channel 316 that matches, in size and shape, the outward perimeter of a corresponding tube (e.g, a 2.66 French, a 3.0 French, 3.5 French, 4.0 French, 5.0 French or 8.0 French tube or other specified tube). In the embodiment as shown, four channels are defined for hold 3.5, 4.0, 5.0 and 8.0 French tubes. Accordingly, the corresponding tube may be inserted into a channel 316 to be held in place at least in part by the tabs 308 and flanges 306.

FIGS. 24 and 25 are cutaway views that illustrate alternative embodiments of the flanges and tabs that define the channels for holding an umbilical catheter. As may be seen, tabs 308 have a planar vertical surface in FIG. 24 and tabs 308 have a round endpoint surface in FIG. 25. One advantage of tabs 308 of FIG. 25 is that the curved shape reduces the likelihood of a tube being damaged while forcibly inserted into the channel 316 defined by flanges 306 and tabs 308.

Figure 26:
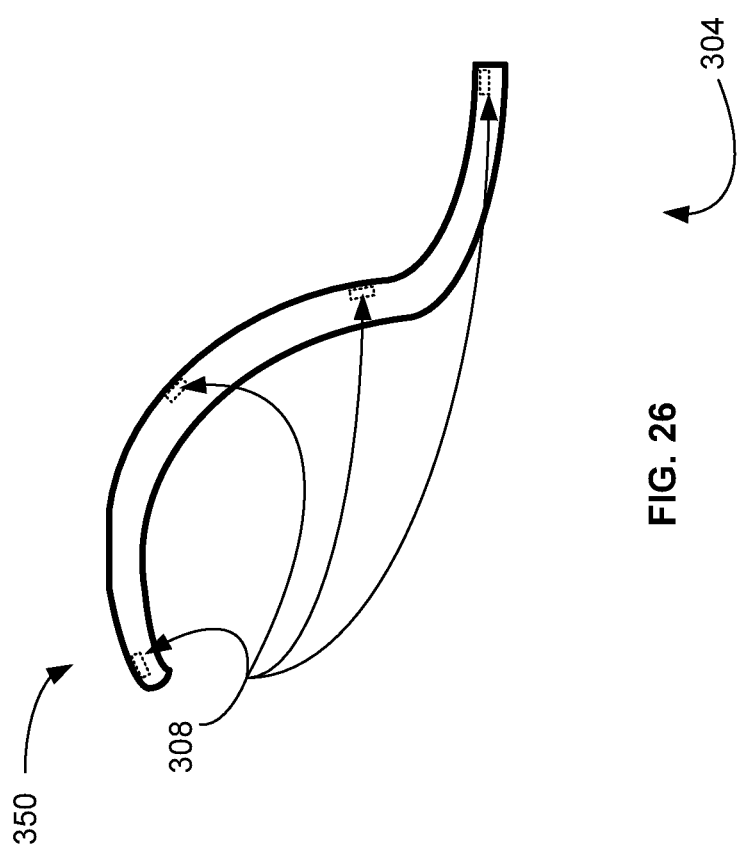
FIG. 26 is an alternative embodiment of a support member that includes an upper end that curves down towards the umbilical stub.

FIG. 26 is an alternative embodiment of a support member 304 that includes an upper end that curves down towards the umbilical stub. Support member 304 includes an upper end 350 that curves down towards the umbilical stub to reduce bend (and not reduce flow rate) of a catheter tube as the tube extends from the support member 304 to the umbilical stub. Support member 304 includes 4 sets of tabs 308 disposed approximately as shown to hold a catheter tube in place. It should be understood that support member 304 may include any of the aspects described in relation to the other figures including defining a plurality of channels to receive a corresponding plurality of tubes or catheters of specified sizes. Further, in an alternative embodiment, tabs 308 may extend a substantial portion of/along support member 304 thereby reducing the total number of tabs.

While the invention is susceptible to various modifications and alternative forms, specific embodiments thereof have been shown by way of example in the drawings and detailed description. It should be understood, however, that the drawings and detailed description thereto are not intended to limit the invention to the particular form disclosed, but, on the contrary, the invention is to cover all modifications, equivalents and alternatives falling within the spirit and scope of the present invention as defined by the claims. As may be seen, the described embodiments may be modified in many different ways without departing from the scope or teachings of the invention. For example, the various exemplary embodiments of the tube securing structures or clamps may readily include features or aspects that are combined with other of the various embodiments of the tube securing structures or clamps without departing from the spirit of the invention.

The invention claimed is:
1. A catheter securing system, comprising:
a base formed of a silicon or plastic matter;
a catheter;
a catheter support member integrally formed with the base that allows the catheter to be inserted into a patient in a relationally secure manner to prevent the catheter from pistoning within an infant when the base is securely affixed to the patient, wherein the catheter support member comprises:
- a first securing element that is aligned substantially vertically that defines at least one channel that holds the catheter substantially vertically in relation to the base; and
- a second securing element that defines at least one channel that is axially disposed in a substantially non-parallel manner in relation to the first securing element; and
- wherein the catheter is securely affixed to the catheter support member by the first and second securing elements.

2. The catheter securing system of claim 1 wherein the catheter support member comprises two upwardly extending support members and a supporting beam member that structurally extends between the two upwardly extending support members.

3. The catheter securing system of claim 2 wherein the supporting beam member comprises a channel that is shaped and sized to receive and securely hold the catheter.

4. The catheter securing system of claim 1 wherein the base comprises four outwardly extending base members.

5. The catheter securing system of claim 1 wherein the base comprises a base portion that can circumvent an umbilical stub.

6. The catheter securing system of claim 5 wherein the base comprises a base ring.

7. The catheter securing system of claim 1 wherein the base comprises two eyelets that allow the catheter securing system to be stitched to the patient.

8. A catheter securing system, comprising:
- a base member defining an aperture that can circumvent an umbilical stub formed of a silicon or plastic matter;
- a tube or catheter;
- a tube support member integrally formed with the base member that allows the tube to be inserted into a baby umbilical cord or stub in a relationally secure manner to prevent the tube from pistoning within an infant wherein the tube support member is configured to securely hold the tube or catheter away from an infant's body; and
- the tube support member comprising a plurality of channels for receiving the tube or catheter of a specified size and for securely holding the tube or catheter wherein at least two of the channels are sized to hold tubes or catheters having different sizes.

9. The catheter securing system of claim 8 wherein at least one channel is sized to receive and holds a 3.0 French scale tube.

10. The catheter securing system of claim 8 wherein at least one channel is sized to receive and holds a 3.5 French scale tube.

11. The catheter securing system of claim 8 wherein at least one channel is sized to receive and holds a 4.0 French scale tube.

12. The catheter securing system of claim 8 wherein at least one channel is sized to receive and holds a 5.0 French scale tube.

13. The catheter securing system of claim 8 wherein at least one channel is sized to receive and holds a 8.0 French scale tube.

14. The catheter securing system of claim 8 wherein the tube support member includes four channels and further wherein at least one channel is sized to receive and holds a 2.66 French scale tube.

15. A catheter securing system, comprising:
- a base formed of a silicon or plastic matter that further includes at least one base member;
- a tube support member integrally formed with the at least one base member that holds a tube or catheter vertically to be directed inserted axially into an umbilical cord or stub in a relationally secure manner to prevent the tube from pistoning within an infant;
- a plurality of outwardly extending flanges that extend from the base; and
- the tube support member comprising at one least channel for receiving the tube or catheter of a specified size and for securely the tube or catheter.

16. The catheter system of claim 15 wherein the base includes a base member defining an aperture that can circumvent an umbilical stub.

17. The catheter securing system of claim 15 wherein the tube support member includes a plurality of channels and further wherein at least one channel is sized to receive and holds at least one of a 2.66, a 3.0, a 3.5, a 4.0, a 5.0 or an 8.0 French scale tube.

18. The catheter securing system of claim 15 wherein base includes a plurality of tabs to facilitate securing the base against the infant.

19. The catheter securing system of claim 15 further including a second tube support member configured to be oriented substantially parallel to a body surface and substantially orthogonal in relation to the tube support member.

* * * * *